United States Patent [19]

Shah

[11] 4,393,881

[45] Jul. 19, 1983

[54] MIDSTREAM URINE COLLECTION DEVICE

[76] Inventor: Nayan S. Shah, 15091 Isleview, Chesterfield, Mo. 63017

[21] Appl. No.: 270,005

[22] Filed: Jun. 3, 1981

Related U.S. Application Data

[63] Continuation-in-part of Ser. No. 78,570, Sep. 24, 1979, abandoned.

[51] Int. Cl.[3] .............................................. A61B 10/00

[52] U.S. Cl. .................................................... 128/760

[58] Field of Search ................................ 128/760–766, 128/771, 295; 141/329; 73/421 R; 4/454, 462, 463, 479

[56] References Cited

U.S. PATENT DOCUMENTS

| | | | |
|---|---|---|---|
| 3,469,572 | 9/1969 | Nehring | 128/764 |
| 4,106,490 | 8/1978 | Spilman et al. | 128/760 |
| 4,116,066 | 9/1978 | Mehl et al. | 128/760 |

*Primary Examiner*—Lee S. Cohen

*Attorney, Agent, or Firm*—Hill, Van Santen, Steadman, Chiara & Simpson

[57] ABSTRACT

A midstream urine collection device (10, 110) includes a urine receiving cup (12) into which a sample of urine is deposited. A barrel (28) is attached to the receiving cup (12) and has a receiving bore (44) therein. A needle assembly (23) is mounted in the barrel (28) in flow communication with the inside of the receiving cup (12). An evacuated container (46) is adapted to be inserted into the receiving bore (44) of the barrel (28) so that a cannula (24) of the needle assembly (23) pierces a plug (50) on the container (46), whereby urine is drawn from the cup (12) into the evacuated container (46). The needle assembly may have a valve (25) closing off the flow through the needle cannula. The valve may be a valve sleeve (26) which also shrouds the end of the needle cannula. The collection device (10, 110) also includes a pair of opposed arms **(16*a*, 16*b*) and a flat portion (38) on a shield (36, 136) carried by the barrel (28), which cooperate to maintain the device (10, 110)** in a stable upright position on a supporting surface.

16 Claims, 6 Drawing Figures

12
10
18
22
23
25
34
28
36
38
16a
16b
20
14
24
26

12
36
14
17
16a
16b 39
36
30
34
40
46
14
19
24
25
28
42
20
21
32
12
13
17
48
38
50
26
16a
15
18
22
23

44
40
36
42
34

38

MIDSTREAM URINE COLLECTION DEVICE

DESCRIPTION

This application is a continuation-in-part of my copending prior application Ser. No. 078,570, filed Sept. 24, 1979, now abandoned.

TECHNICAL FIELD

This invention relates to a urine collection device for obtaining a urine sample without contamination of either testing personnel or of an evacuated container into which the urine is transferred.

BACKGROUND ART

One prior urine collection device, such as shown in U.S. Pat. No. 4,116,066, utilizes a cannula located at the bottom of the specimen cup with the beveled distal end pointing upwards. The cup has a slot near the bottom through which the urine may pass into the proximal end of the cannula. An evacuated tube is inverted and is pushed down over the cannula so that the cannula extends through an end plug and into the evacuated tube. In this position the end plug rests against a shoulder located above the level of the urine in the cup. The pressure differential between the outside air and the evacuated tube forces the urine to fill the tube.

Another urine collector, as disclosed in U.S. Pat. No. 4,106,490, utilizes a hollow body in conjunction with a specimen container, such as a centrifuge tube, and an excess urine outlet. The excess urine outlet is effectively sized and selectively spaced from the specimen container to assure sufficient flow into the specimen container while enabling the remainder to be drained away.

Although these apparatus effectively permit urine to be collected for testing, there is the possibility of contamination of the testing personnel or of the specimen tube. In the first apparatus, this can occur when the urine is poured into the specimen cup, thereby contaminating the shoulders against which the end plug rests. In the second apparatus, the centrifuge tube is an open container and therefore is subject to accidental spilling of the contents.

It is desirable to provide a urine collection device which minimizes the possibility of contamination of either the testing personnel or of the evacuated container. This is particularly important when many tests over a period of time are to be performed by testing personnel or where the testing is to be performed by the patient himself.

DISCLOSURE OF THE INVENTION

The present invention is directed to overcoming the problem as set forth above.

According to the present invention, a midstream urine collection device for obtaining a urine sample without contamination of testing personnel or of an evacuated container into which the urine is transferred includes an open receiving cup into which the urine sample is deposited. An elongate transparent barrel, capable of receiving an evacuated container, is mounted adjacent the receiving cup and projects upwardly at an angle to a supporting surface upon which the device is placed. A communicating channel and a connecting hub with a needle assembly attached extend from the receiving cup into the barrel. In one form of the invention, a valve is provided on the needle assembly to prevent leaking of urine into the barrel when the valve is closed.

In another form of the invention, the open end of the needle is situated above the highest point of the receiving cup to prevent urine from leaking into the barrel when the cup is full. An evacuated container containing testing chemicals or other like substances and having a self-sealing and plug is inserted into the barrel in alignment with the needle assembly. As the evacuated container is pressed into the barrel the cannula of the needle assembly is inserted through the end plug and into the evacuated chamber, whereupon urine is drawn from the receiving cup into the evacuated container. Arms on the receiving cup and a shield member on the barrel cooperate to support the collection device in a generally upright position.

BEST MODE FOR CARRYING OUT THE INVENTION

Figure 1:
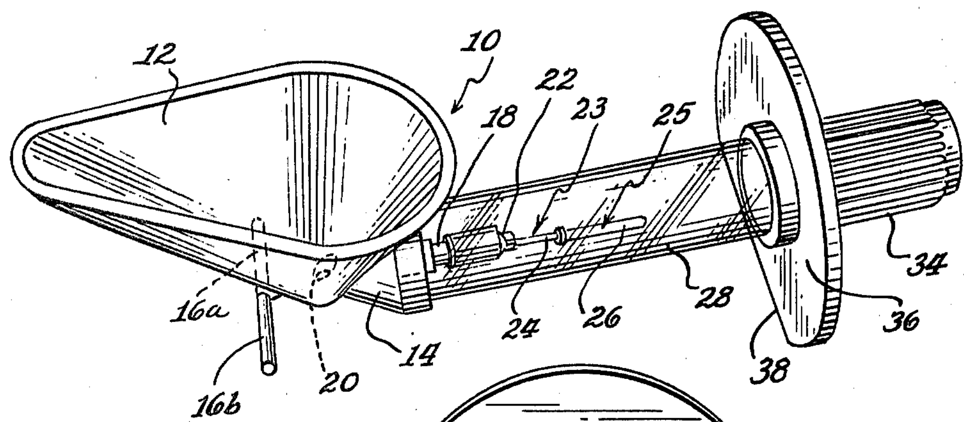
FIG. 1 is a perspective view of one form of a urine collection device of the present invention.
Figure 2:
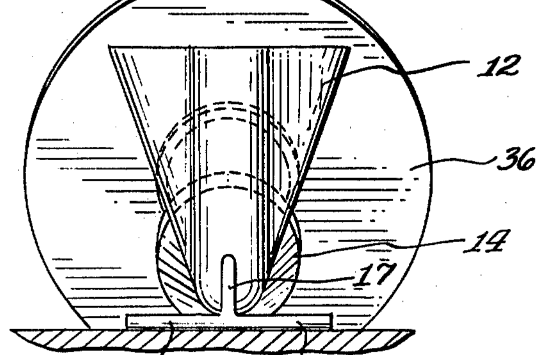
FIG. 2 is an end view of the urine collection device of FIG. 1.
Figure 4:
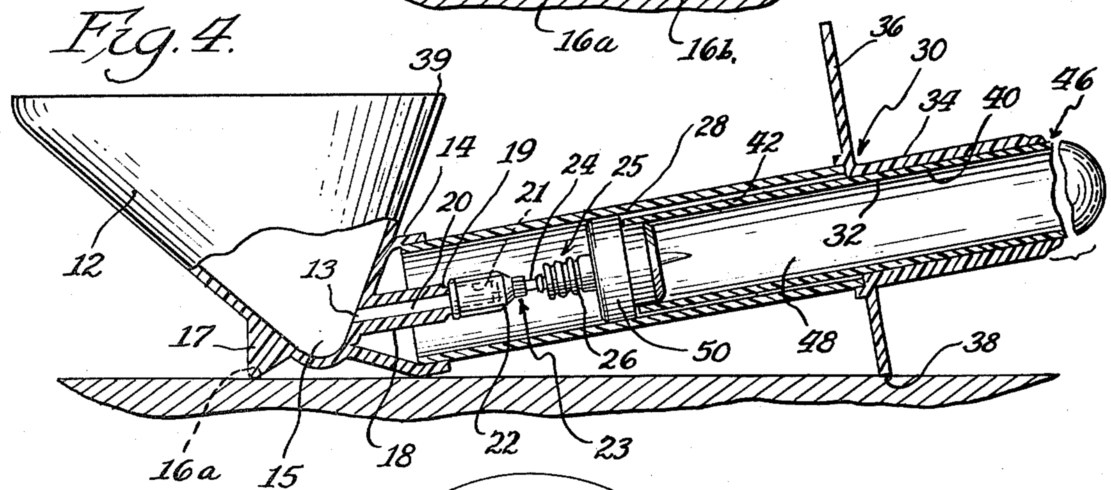
FIG. 4 is an elevational view partially in section, showing an evacuated container inserted into the barrel.
Figure 3:
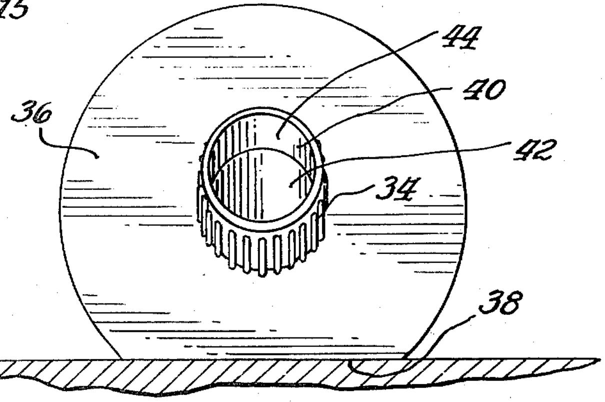
FIG. 3 is an end view of the urine collection device of FIG. 1.

Referring to the one form of the invention shown in FIGS. 1–4, the midstream urine collection device 10 includes a urine-receiving cup 12 into which a sample of urine is deposited. The receiving cup 12 is generally tear-shaped in horizontal cross section and V-shaped in vertical cross section so as to provide ease in collecting a specimen in the cavity thereof and to direct the specimen toward an outlet 13. The receiving cup 12 has a barrel collar 14 integrally formed on one side of its lower end portion 15, which collar opens outwardly and at a slight angle upwardly therefrom. A pair of opposed arms **16*a* and 16*b* are located on said lower end portion 15 of the receiving cup 12 in spaced relation to said barrel collar 14. The arms 16*a*, 16*b*, in the illustrated embodiment, are integrally formed on an embossment 17 formed on said cup 12. Extending from the cup 12 and concentric with the barrel collar 14 is a connecting sleeve 18 having a tapered hub 19 on the outer end thereof. A communicating channel 20 extends through the sleeve 18 and hub 19 from the lower portion 15 of the receiving cup 12**.

Engaging with the tapered hub 19 and sealed so as to make a liquid-tight fit is a tapered socket 21 of a hub 22 of a needle assembly 23. Any appropriate connection between the needle assembly 23 and the sleeve 18 is contemplated. The needle assembly 23 may be separate, as illustrated, or may be formed integrally with the sleeve 18 without departing from the invention. The needle assembly 23 has a cannula 24 seated in the hub 22 with value means, exemplified by a valve 25, closing off flow through the cannula. As illustrated, the valve 25 is a collapsible closed end sleeve 26 made of elastic material fitted over the distal end of the cannula 24. A typical sleeve valve is shown and described in U.S. Pat. No. 3,469,572 to J. R. Nehring. The value sleeve 26 is penetrated by the distal end of the cannula 24 and opens when it is collapsed longitudinally to expose the bevel of the cannula 24. The value sleeve 26 will reseal the opening in the cannula 24 when the pressure that collapsed the valve longitudinally is removed.

A barrel 28, made of transparent material, is attached to the receiving cup 12 by attaching one end portion of the barrel 28 in the barrel collar 14. The barrel 28 encircles the needle assembly 23 and extends at an angle upwardly from a supporting surface for the device. The longitudinal axis of the needle assembly 23 substantially coincides with the longitudinal axis of the barrel 28. A shield and gripping member 30 is fastened to the outer end 32 of the barrel 28 with a ribbed gripping portion 34 extending outwardly from a transverse disc-shaped shield portion 36. The gripping portion 34 has a bore 40 aligned with the inside surface 42 of the barrel 28 to form a receiving bore 44. The shield portion 36 extends transverse to the gripping portion 34 and has a flat portion 38 on the lower edge of the shield, which flat portion 38 lies in a common plane with the common axis of the opposed arms 16*a* and 16*b*. When the flat portion 38 and the arms 16*a*, 16*b* engage a supporting surface, opening-defining edge 39 of the cup 12 lies substantially parallel to the supporting surface, and the longitudinal axis of the receiving bore 44 in the barrel 28 lies at an acute angle to said supporting surface. The acute angle facilitates insertion and removal of an evacuated container 46.

The evacuated tube or container 46 may be of the type that is well known in the blood-collecting art as a "Vacutainer" (Trademark of the Becton-Dickenson Company) and is described in U.S. Pat. No. 2,460,641 to J. J. Kleiner. The container 46 is comprised of an elongate tubular vessel 48 closed at one end and having a plug or stopper 50, made of rubber or the like, sealing the other end. The vessel 48 can contain any one of several different desirable testing mediums, for instance, to indicate concentration of glucose. Either a reagent strip, which changes color in the presence of glucose, or a lyophylized reagent that reacts with glucose to produce a color change, is placed in the vessel 48 prior to evacuating the vessel 48 and sealing same with the plug or stopper 50. The tube or container 46 is adapted to be inserted in the receiving bore 44 of the barrel 28 and gripping portion 34 with the plug or stopper 50 aligned with the valve 25 on the needle assembly 23. The material of the plug or stopper 50 is such that it will seal around the cannula 24 of the needle assembly 23 as the cannula 24 penetrates the plub 50 and it will seal itself when the cannula 24 is withdrawn from the plug 50.

Figure 5:
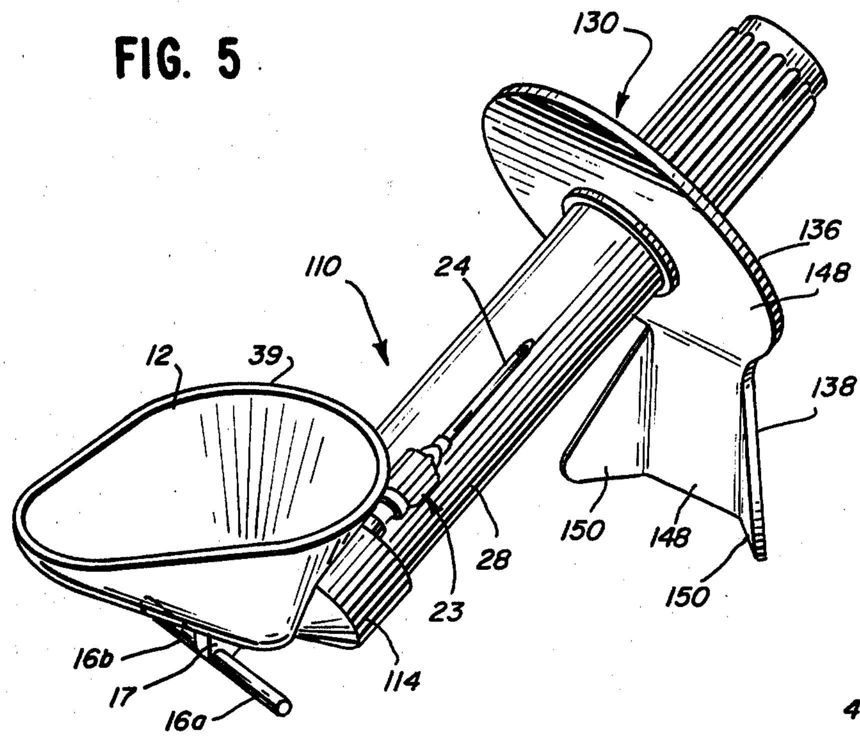
FIG. 5 is a perspective view of a modified form of a urine collection device; and, FIG. 6 is an elevational view partially in section, showing an evacuated container inserted into the barrel of the modified collection device.
Figure 6:
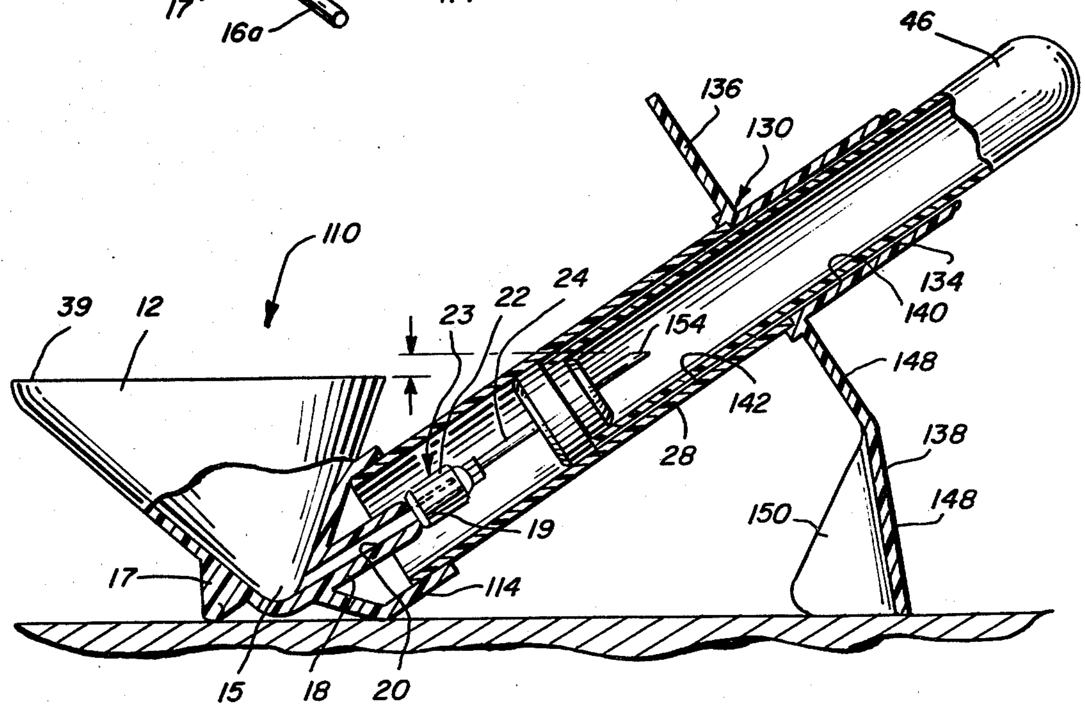

In FIGS. 5 and 6, a modified form of midstream urine collection device 110 is shown, wherein the receiving cup 12 has the upwardly facing edge 39 at its top, defining an opening into the cavity provided by the cup, and the cup has the downwardly directed embossment 17 with the sidewardly, and oppositely, extending arms 16*a* and 16*b*. A barrel collar 114 is integrally formed on one side of the lower portion 15 of the cup. The collar 114 opens outwardly and upwardly at a fairly substantial angle to the horizontal. Extending from the lower end portion 15 of the cup 12 and concentric with the barrel collar 114 is a connecting sleeve 18 having a tapered hub 19 on the outer distal end thereof. A communicating channel or passageway 20 extends from the interior of the cup 12 through the sleeve 18 and hub 19. Engaging with the tapered hub 19 and forming a liquid tight fit thereto is a tapered socket 21 of a hub 22 of a needle assembly 23. The needle assembly 23 includes a cannula 24 attached to the hub 22. Any appropriate connection between the needle assembly 23 and the sleeve 18 is contemplated so that the needle assembly 23 may be removable from the sleeve 18 as shown, or may be permanently affixed on the sleeve.

A barrel 28, made of transparent material is attached to the barrel collar 114 by resting in the open mouth of the collar 114. The barrel 28 encircles the needle assembly 23 and cannula 24. The axis of the needle assembly 23 and of the barrel 28 substantially coincide with each other. A shield and gripping member 130 is fastened to the outer end portion of the barrel 28 and has an axis which, once again, substantially coincides with the axes of the needle assembly 23 and barrel 28. The member 130 has a shield portion 136 and a gripping portion 134 with a bore or opening 140 through the gripping portion 134 in alignment with the bore or opening 142 in the barrel 28. The shield portion 136 serves a dual function in that not only does it have a circular body portion 148 that affords some protection against splash, but also it has an angled tri-part support portion 138. The support portion 138 has a center part 146 integrally formed with and angularly disposed with respect to the body portion 148 of the shield and includes a pair of bent wing parts 150, one on each side of said center part 146. The wing parts 150 are angled with respect to the center part 146 with both wing parts 150 and the center part 146 having a common bottom edge 152. The support portion 138 of the member 130 is such that with the device 110 resting on a support surface, the opening 154 of the needle cannula 24 will be above the plane of the open end 39 of the cup 12.

As is particularly illustrated in FIG. 6, the axes of the collar 114, the barrel 28 and the gripping portion 134 of the member 130 all coincide and lie at an angle with respect to the supporting surface substantially larger than the angle of the comparable elements of the form of invention shown in FIGS. 1–4. The angle of the collar 114, the barrel 28 and the member 134 is such that with the device resting on a support surface the open end 154 of the cannula 24 is at an elevation relative to the top of the cup 12, such as, but not limited to, above the plane of the open edge 39 of the receiving cup 12, so that a fluid sample poured into the receiving cup will not run out through the needle cannula 24 and into the barrel 28.

An evacuated container 46, such as described above with respect to the form of invention shown in FIGS. 1–4 is provided and is inserted, stopper 50 first, into the barrel 28. The stopper 50 can be partially impaled on the needle cannula point, enough to plug the needle cannula passageway to the cup but not enough to release the vacuum. Thereafter, with a sample in the cup, a very short push on the container 46 permits the needle cannula to penetrate into the evacuated portion of the container 46 whereupon the sample is drawn into the tube or container 46.

INDUSTRIAL APPLICABILITY

In operation of the invention as shown in FIGS. 1–4, a midstream urine sample is first obtained and is deposited into the receiving cup 12, preferably with the arms 16*a*, 16*b* and flat 38 of the device 10 resting on a supporting surface. An evacuated container 46 containing the appropriate testing medium is inserted into the upwardly directed receiving bore 44 with the end plug 50 pointing into the barrel 28. The receiving bore 44 is sized so as to guide the end plug 50 of the evacuated container 46 into alignment with the valve 25 and cannula 24. The plug 50 causes the distal end of the cannula 24 to penetrate the valve 25 and to expose the distal end of the cannula 24 to the plug 50. The valve 25 is collapsed as the evacuated container 46 is further inserted into the barrel 28 until the opening in the cannula 24 is exposed to the vacuum inside the evacuated container 46. The pressure differential between the atmospheric pressure acting on the urine in the cup 12 and the vacuum within the container 46 forces the urine to travel through the communicating channel 20, through the needle assembly 23 and into the evacuated container 46. The evacuated container 46 may contain a test strip which changes color, for example, when glucose is present in the urine. In the alternative, the evacuated container 46 may contain a lyophylized reagent that reacts with glucose to produce a color change, thereby providing an indication of glucose in the urine. The barrel 28 is transparent so that the testing personnel can observe the filling and initial reaction on the urine in the container.

Once the evacuated container 46 is filled with urine, the closed end of the container 46 extending beyond the gripping portion 34 is grasped and pulled to remove the container 46 from the receiving bore 44. The plug 50 on the evacuated container 46 reseals itself when it is removed from the cannula 24. The plug 50 somewhat wipes the outer surfaces of the cannula 24 as the cannula is removed from the plug 50 thereby minimizing contamination of the external surfaces of the plug 50 and of the external surfaces of the evacuated container 46. The valve 25 will automatically reseal the opening in the cannula 24 and will re-enclose the outer surfaces of the cannula 24 without contaminating the receiving bore 44 of the barrel 28. Since none of the external surfaces of the container 46 has been exposed to contamination, the testing personnel are likewise not exposed to contamination. Even though the barrel 28 protects the testing personnel from contact with the needle assembly 23, contamination of the personnel by said needle assembly 23 is minimal due to the valve 25 closing off and shielding the distal end of the cannula 24.

The opposed arms **16*a* and 16*b* extend transversely to the axis of the receiving bore 44 and parallel with the flat portion 38 on the enlarged shield portion 36 to cooperate to support the collection device 10 in a generally upright position on a supporting surface. The shield portion 36 also acts as a shield to divert any urine that may be splashed from the collection cup 12 during filling and removing of the containers 46 from the barrel 28. Also, the shield portion 36 protects a person's hand when the device is being carried. The grasping portion 34 may therefore be used, not only to steady the device during the drawing of samples into the containers 46, but also as a handle to carry the collection device 10** in a convenient manner without contamination.

The device may be provided as a kit wherein one device 10 would be provided with several sample containers 46 and several needle assemblies 23. After each sample is drawn, the needle assembly 23 is removed, the cup 12 and channel 20, as well as associated parts, are washed and dried, and a new needle assembly 23 installed ready for the next sample. A long hollow rod with a hub gripping end portion is used as a wrench and as an installation tool to remove and to affix the new needle assemblies 23 onto the hub 19.

The modified form of invention shown in FIGS. 5 and 6, has the end of the needle cannula located so that the fluid in the cup will not flow through the needle into the barrel without assistance. As shown, the end of the needle cannula is above the plane of the open end of the cup 12. However, it is possible that the end of the needle cannula can be in the plane of or slightly below the plane of the end of the cup 12 without free flow of fluid being established through the needle cannula and, as such, as within the scope of the invention.

In either form of the invention, a sample is placed in the cup 12 and is drawn into an evacuated container 46 by pressing the container into the barrel until the needle cannula penetrates into the evacuated chamber in the container. It is contemplated that any structure that prevents free flow of fluid from the sample cup into the barrel is serving as a valve means. Impaling the stopper 50 of the tube or container 46 upon the needle cannula, placing a constriction in the passageway communicating with the sample cup and the like, serve to stop the free flow of fluid into the barrel so that the barrel and subsequently the tube or container 46 are not contaminated by contact with the fluid. In either form of the invention, the needle means assembly 23 is so constructed and related to the cup 12 that fluid (urine) sample poured into the cup will be substantially precluded from free flow through the cannula 24 unless flow is induced therethrough.

The barrel 28 and gripping portion 34, 134 may be grasped in the hand of a patient, and used as a handle to hold the cup 12 in position to receive a sample. The tube or container 46, which had previously been slid into the barrel 28, may then be pushed onto the needle whereupon a sample is drawn. The filled tube 46 may be then removed and the device 10, 110 is discarded because it is adapted to be produced in quantity at low cost as a throwaway item, although it may be conventionally sterilized or otherwise cleaned for reuse, if desired.

Other aspects, objects and advantages of this invention can be obtained from a study of the drawings, the disclosure and the appended claims.

I claim:

1. A midstream urine collection device (10) comprising:

- a receiving cup (12) having a fluid receiving cavity with an opening therein;
- support means (**16*a*, 16*b*) carried by said cup (12) and engageable with a support surface to retain said cup (12**) with the opening facing upwardly away from said support surface;
- a needle assembly (23) carried by a lower portion of said cup (12) and extending outwardly away from the fluid receiving cavity in said cup, a channel (20) communicating between said cup (12) and said needle assembly (23); and
- valve means (25) on said needle assembly (23) controlling the flow of fluid through said needle assembly (23).

2. A urine collection device as claimed in claim 1, wherein an elongate barrel member (28) is secured to said cup (12) and concentrically surrounds said needle assembly (23).

3. A urine collection device as claimed in claim 2, wherein a collar (14) is formed on said cup (12) and said barrel member (28) is secured to said collar (14).

4. A urine collection device as claimed in claim 2, wherein a shield means (36) is carried by said barrel member (28), said shield means (36) has a flat edge (38)

on one side thereof, said flat edge (38) lies parallel to the support means (16*a*, 16*b*) for supporting said cup (12) in the open upward condition and for directing the longitudinal axis of the barrel member (28) at an acute angle to said support surface.

5. A urine collection device as claimed in claim 4, wherein an evacuated container (46) having a puncturable stopper (50) is removably inserted in said barrel member (28) in alignment with said needle assembly (23), and wherein a fluid sample in said cup (12) is drawn into said container (46) by urging said stopper (50) onto the point of the needle assembly (23) to open the valve means (25) and to draw the fluid sample into the container (46).

6. A midstream urine collection device (10) comprising:

a receiving cup (12) having a cavity therein, said cup having an opening into said cavity;

an elongate cylindrically-shaped barrel member (28) secured to an exterior portion of said cup (12) and extending outwardly therefrom;

support means (16*a*, 16*b*) carried by said cup (12) and engageable with a support surface to retain said cup (12) with the opening facing upwardly away from said support surface;

a needle assembly (23) carried by a lower portion of said cup (12) and being located centrally of said barrel member (28), a channel (20) communicating between the cavity in said cup (12) and said needle assembly (23); and valve means (25) on said needle assembly (23) controlling the flow of fluid through said needle assembly (23).

7. A urine collection device as claimed in claim 6, wherein a shield means (36) is carried by said barrel member (28), said shield means (36) has a flat edge (38) on one side thereof, said flat edge (38) lies parallel to the support means (16*a*, 16*b*) for supporting said cup (12) with the opening facing upward and for directing a longitudinal axis of the barrel member (28) at an acute angle to said support surface.

8. A midstream urine collection device (10) comprising:

a receiving cup (12) having a cavity with an opening therein, a laterally directed collar (14) integrally formed on said cup, a hub (19) carried by said cup (12) and projecting outwardly from within the confines of said collar (14), a channel (20) communicating between the cavity in said cup (12) and said hub (19);

an elongate cylindrically-shaped barrel member (28) secured to said collar (14) and surrounding said hub (19);

shield means (36) carried by one end portion (32) of said barrel member (28), said shield means (36) having a flat edge (38) for engaging a support surface;

support means (16*a*, 16*b*) extending transversely to said cup (12) and lying generally parallel to said flat edge (38) on said shield means (36) and cooperating therewith to retain said barrel member (28) in an angularly upwardly disposed direction and to retain said cup (12) with the opening facing upward away from said support surface;

a needle assembly (23) having a hub (22) on one end portion engaging with the hub (19) in said collar (14) and having a tapered point on the other end portion;

valve means (25) on said needle assembly (23) controlling the flow of fluid through said needle assembly (23); and an evacuated container (46) having a puncturable stopper (50) which is removably inserted in said barrel member (28) in alignment with said needle assembly (23), whereby a fluid sample in said cup (12) can be drawn into said container (46) by urging said stopper (50) onto the point of the needle assembly (23) to open the valve means (25) and to draw the fluid sample into the container (46).

9. A midstream urine collection device (10, 110) comprising:

a receiving cup (12) having a cavity therein, said cup having an opening into said cavity;

support means (16*a*, 16*b*) carried by said cup (12) and engageable with a support surface to retain said cup (12) with the opening facing upwardly away from said support surface;

an elongate cylindrically-shaped barrel member (28) secured to an exterior portion of said cup (12) and extending outwardly and upwardly therefrom;

a needle means (23) carried by a lower portion of said cup (12) and located centrally of said barrel member (28), said needle means (23) comprising a tapered point cannula (24) projecting outwardly and upwardly from said lower portion of said cup (12);

a channel (20) communicating between the cavity in said cup (12) and said cannula (24); and said needle means (23) being so constructed and related to said cup (12) that urine sample poured into said cup cavity will be substantially precluded from free flow through said cannula unless flow is induced therethrough.

10. A urine collection device as claimed in claim 9, wherein an evacuated container (46) having a puncturable stopper (50) is removably inserted in said barrel member (28) in alignment with said needle means (23), and wherein urine sample flow through said needle means from said cup (12) is adapted to be effected into said container (46) by urging said stopper (50) onto the point of the needle means (23) to draw the fluid sample into the container (46).

11. A urine collection device as claimed in claim 9, wherein said point on said needle means is located in a plane substantially coinciding with a plane containing the opening into said cup.

12. A urine collection device as claimed in claim 9, wherein an evacuated container (46) having a puncturable stopper (50) is positioned in said barrel member (28) with the point embedded in said stopper (50) but not penetrating said stopper.

13. A device according to claim 9, including shield means (36, 136) cooperating with said support means (16*a*, 16*b*) for maintaining the device in a stable upright position on said support surface.

14. A device according to claim 13, wherein said shield means (36, 136) comprises a shield mounted on said barrel member (28).

15. A device according to claim 14, including a gripping portion (34) associated with said shield means (36, 136).

16. A device according to claim 15, wherein said gripping portion (34) comprises a tubular extension of said barrel member (28).

* * * * *